United States Patent [19]

Lentrichia et al.

[11] Patent Number: 4,721,681
[45] Date of Patent: Jan. 26, 1988

[54] IMMUNOASSAY IN CENTRIFUGAL FIELD WITH COMPLEMENTARY PARTICLES OF DIFFERING SPECIFIC GRAVITIES

[75] Inventors: Brian B. Lentrichia, Mahwah, N.J.; Michael F. Turanchik, Stony Point; Linda A. Kish, Larchmont, both of N.Y.

[73] Assignee: Fisher Scientific Company, Pittsburgh, Pa.

[21] Appl. No.: 733,689

[22] Filed: May 14, 1985

[51] Int. Cl.[4] ................. G01N 33/557; G01N 33/543; G01N 33/551; G01N 33/546

[52] U.S. Cl. ..................................... 436/523; 436/517; 436/518; 436/524; 436/531; 436/534; 436/805

[58] Field of Search ............... 436/514, 517, 518, 523, 436/524, 531, 533, 538, 805, 534

[56] References Cited

U.S. PATENT DOCUMENTS

| | | |
|---|---|---|
| 4,115,535 | 9/1978 | Giaever . |
| 4,118,192 | 10/1978 | Sawai et al. . |
| 4,184,849 | 1/1980 | Cambiaso et al. ................... 436/523 |
| 4,191,739 | 3/1980 | Uzqiris et al. . |
| 4,202,665 | 5/1980 | Wenz et al. . |
| 4,205,954 | 6/1980 | Babson . |
| 4,279,617 | 7/1981 | Masson et al. . |
| 4,308,026 | 12/1981 | Mochida et al. . |
| 4,459,361 | 7/1984 | Gefter ................................. 436/523 |
| 4,481,298 | 11/1984 | Cone, Jr. et al. . |
| 4,687,636 | 8/1987 | Hart ................................. 436/807 X |

OTHER PUBLICATIONS

"High Density Latex for Microtitration Use", M. Kariya, et al., pp. 4–12.
"JSR High Density Uniform Latex for Diagnostic Reagents", Japan Synthetic Rubber Co., Ltd., pp. 1–6.
Wenz, B. et al., Clin. Chem., 25 No. 9:1613–1616 (1979).

*Primary Examiner*—Robert J. Warden
*Assistant Examiner*—Jack Spiegel
*Attorney, Agent, or Firm*—Alan M. Doernberg

[57] ABSTRACT

Competitive or inhibition assays are disclosed in which sample (e.g., containing target antigen), a reagent containing first particles (e.g., antibody-coated light particles) and a reagent containing second particles (e.g., antigen coated heavy particles) are reacted in a centrifugal field. Differential migration of first particles, of second particles and of first particles linked to second particles leaves a concentration of particles at a locus in solution after a time, which concentration is a function of the analyte concentration in the sample.

18 Claims, No Drawings

IMMUNOASSAY IN CENTRIFUGAL FIELD WITH COMPLEMENTARY PARTICLES OF DIFFERING SPECIFIC GRAVITIES

The present invention relates to immunoassays and other assays for binding pair members of the type involving particles coated with other binding pair members. In particular, the present invention relates to such assays performed in a centrifugal field such as on a microcentrifugal analyzer.

Agglutination assays, in particularly immunoassays, are well-known in several forms. In direct tests, antibodies coated on particles such red blood cells or synthetic polymeric particles (e.g., polystyrene latex) are mixed with a sample and clump in the presence of a sufficiently large concentration of target antigen which can be bound by antibody on more than one particle. Inhibition agglutination assays involve determining the concentration of target antigen or hapten by its effect in inhibiting a subsequent reaction in which limiting amounts of dissolved multifunctional antibody clump antigen-coated particles. In competition assays, the effect is upon a simultaneous reaction. In other agglutination assays, the target antigen or antibody reacts with particles coated with its complement to form immune complexes; and a dissolved antibody against immune complexes (e.g., rheumatoid factor) causes clumping in an amount proportional to the target binding member.

A variety of proposals have been made to automate agglutination assays, thereby enabling an automated light measurement to serve in place of visual observation to determine the extent of clumping. Examples include U.S. Pat. No. 4,205,954 to Babson (1980) and various patents to Sawai, et al. including U.S. Pat. No. 4,118,192 (1978). Application of such agglutination assays to a centrifugal field (e.g., in a microcentrifugal analyzer) is disclosed in U.S. Pat. No. 4,202,665 to Wenz, et al.

In other forms of immunoassays, the target binding member is assayed by reaction either successively or concurrently with an immobilized binding pair member and a labeled reagent binding pair member. In the competition mode, for example, when one is analyzing for a hapten or antigen, the analyte hapten or antigen competes with labeled hapten or antigen for a limiting number of sites on immobilized antibody. By washing away unbound binding members, the label remaining on the immobilized antibody is an inverse function of the analyte concentration. In the inhibition mode, analyte hapten or antigen reacts with immobilized antibody before labeled hapten or antigen is introduced. In the sandwich mode, the target antigen or antibody forms a bridge between an immobilized antibody or antigen, respectively, and a labeled antibody or anti-antibody, respectively. By washing away unbound labeled moiety, the label remaining is a positive function of the concentration of target antigen or antibody. In certain cases, particles have been used as a convenient form of solid substrate for the immobilization of the antibody or antigen in such tests. See U.S. Pat. Nos. 4,332,783 to Pernice et al., (sandwich mode); 4,481,298 to Cone, Jr. (sandwich employing two antibodies). In some cases washing the solid phase is a way of separating unbound binding members (and especially unbound labeled reagent binding member) from the solid phase. Centrifugation could be used in such washing. See U.S. Pat. Nos. 4,191,739 to Uzgiris et al.; and 4,115,535 to Giaver, each of which involves a sandwich assay with antigen on both separable and detectable particles.

In comparing the two types of assays described above, it should be apparent that agglutination assays have the advantage of relatively simple reagents and a relatively simple measurement of light density or light scattering. They have the disadvantage, however, of requiring sufficient multifunctionality of the antigen or antibody to cause agglutination (clumping) rather than mere attachment. The assays based upon an immobilized binding pair member and a labeled binding pair member have the advantage of not requiring multifunctionality (mere binding is sufficient). They suffer, however, from the disadvantages of having to attach a detectable label reproducibly to a binding pair member and having to design the instrumentation for the detection of the label which, in many instances, is more complex than the measurement of light scatter or optical density. In the case of microcentrifugal analyzers, particularly, because of in their general use in clinical chemistry measurements, provision is already made for optical density measurements, light scatter measurement or both.

BRIEF DESCRIPTION OF THE INVENTION

The present invention involves a competition or inhibition assay method employing particles of different specific gravities and requiring neither labels (other than the particles themselves) nor sufficient multifunctionality to cause agglutination. The present invention enables a variety of measurements, especially made in the centrifugal field such as in a microcentrifugal analyzer, in which the detecting step can be performed by simple optical density measurement or light scatter measurement. Accordingly, the present invention provides a method for the determination of a target binding pair member in a biological sample which comprises the steps:

(a) reacting in a liquid phase in a chamber in a centrifugal field:
 (i) the sample to be analyzed,
 (ii) a plurality of first particles bearing on their surface a binding pair member complementary to target binding pair member, and
 (iii) a plurality of second particles bearing on their surface a binding pair member competitive with the target binding pair member for binding sites on the complementary binding pair member; the specific gravity of the first and second particles being sufficiently different with respect to the centifugal field and the specific gravity and viscosity of the liquid phase to cause detectably different rates of migration in the centrifugal field for first particles, for second particles and for first particles bound to second particles;
(b) detecting the concentration of particles at a radial locus in the chamber after a specified time of reaction and centrifugation; and
(c) correlating the concentration of particles over time with concentration measured when samples of known target binding member concentration are reacted in the centrifugal field with the plurality of first particles and plurality of second particles.

DETAILED DESCRIPTION OF THE INVENTION

The method of the present invention may be practiced in a centrifugal analyzer and especially a microcentrifugal analyzer. Rotors for such instruments in which the centrifugation, mixing and light measurement occurs are described in U.S. Pat. Nos. 4,226,531 of Tiffany et al., and 4,314,970 of Stein et al. and in copending, commonly assigned U.S. Ser. No. 615,401 of Tiffany et al., filed May 31, 1984. Such rotors define a plurality (e.g., 20 or 40) radially extending cuvettes, each divided by a ramp or dam. The loading part for the first (inner) chamber is typically used to load sample and optionally diluent or additional reagents. The loading port for the second (outer) chamber is typically used to load a reagent or reagents. In use, the initial high rotor speed causes the sample (and reagents, if any) in the first (inner) chamber to overflow the dam and mix with the reagent in the second (outer) chamber. Subsequent mixing while centifuging (typically at a slower rate than the initial burst) causes various reactions to occur, the results of which are monitored at a locus (the light path) within the second (outer) chamber. The use of such apparatus for agglutination assays is described by U.S. Pat. No. 4,202,665 to Wenz et al.

For the present invention, the two types of particles contain complementary binding pair members and the sample is targeted for a binding pair member complementary to the member on the first particles, but competitive with the member on the second particles. The following permutations are then possible:

|   | Inner Port | Outer Port | Type of Assay |
|---|---|---|---|
| 1. | First Particles Sample | Second Particles | Inhibition |
| 2. | Second Particles Sample | First Particles | Competition |
| 3. | First Particles | Second Particles Sample | Competition |
| 4. | Second Particles | First Particles Sample | Inhibition |

In each case, either first particles or second particles will have specific gravities different from that of the liquid phase (generally heavier than the liquid phase), and the other particles will have specific gravity equal to or at least significantly more nearly equal to that of the liquid phase. The density of the liquid phase is generally near 1.0 g/ml, but can be adjusted with additives e.g., sucrose.

In Examples 1-3, below, heavy particles with antigen and light particles with antibody were used to analyze for antigen or hapten. In such case, an inhibition assay was performed (case 1, above) by introducing the light, first particles with the sample into the inner chamber where they can react. After accelerating, both mix with heavy, second particles in the outer chamber. Sample antigen bound to antibody on the light, first particles inhibits subsequent binding antigen on heavy second particles.

By reversing the points of introduction of first and second particles (case 2, above), no reaction will now occur in the inner chamber between sample antigen and antigen on the second, heavy particles. Upon acceleration, both will overflow the dam into the outer second chamber and compete for antibody sites on the first, light particles.

In either case, after some or complete immunochemical reaction, centrifugation will cause the heavy particles and any light/heavy combinations to migrate outward in the centrifugal field. By waiting until such particles have migrated outwardly beyond the light path locus, only a concentration of light particles should remain in the light path. By taking a single endpoint measurement, a value can be obtained (typically of absorbance, but light scattering may be measured instead) functionally related to the concentration of light particles remaining in the light path. Whether the first particles are light or heavy, this value should decline as the concentration of analyte increases. For any particular set of reagents and permutation of introduction (competition or inhibition) this value can be compared with a dose response curve generated with standards of known analyte concentrations.

In some forms of the present invention the liquid phase has substantially the same specific gravity as one of the first and second particles, and has substantially greater specific gravity than the other of the first and second particles. In such embodiments, the other of the first and second particles floats away from the locus (of detectional) inwardly in the centrifugal field. The particles with substantially the same specific gravity remain at the locus except if bound by such other particles.

While the method of the present invention is particularly applicable to apparatus such as a microcentrifugal analyzer wherein the mixing, reacting, migrating and detecting all occur in a centrifugal field (of sometimes varying strength), it is not so limited. One may, for example, conduct the mixing, reacting and migrating in a centrifuge tube spun only after mixing. Detecting can then occur in the stationary tube or by aspirating an aliquot of the supernatant and then subjecting it to optical measurement (e.g., in a spectrophotometer) as in example 4, below.

Various permutations of binding member on first and second particles are also contemplated such as:

| Target Analyte | First Particles | Second Particles |
|---|---|---|
| Antigen | Antibody | Antigen/Hapten |
| Hapten | Antibody | Antigen/Hapten |
| Antibody | Antigen/Hapten | Antibody |
| Nucleic Acid Sequence | Complementary Nucleic Acid Sequence | Homologous Nucleic Acid Sequence |
| Biotin | Streptavidin | Biotin |

Any of the antigens, antibodies or hapten of clinical signficance, including theraputic drugs and drugs of abuse, hormones, proteins, receptors and nucleic acid sequences, may be so assayed.

EXAMPLE 1

Purified human chorionic gonadotrpin(hCG) was covalently coupled to high density latex spheres (specific gravity=1.45) of 1.02 micron average diameter by using a carbodiimide coupling reagent. Mouse monoclonal anti-hCG of high affinity was passively adsorbed onto 0.42 micron diameter latex spheres of low density (specific gravity=1.05). All latex reagents used in this example were suspended in 1% BSA in PBS containing 0.1% sodium azide (suspending medium).

In the sample chamber of a cuvette rotor from a Mutistat III microcentrifugal analyzer made by Instrumentation Laboratories was placed 10 microliters of a 1% (w/w) suspension of antibody-sensitized latex particles along with 45 μl of normal male serum with or without added hCG. The reagent chamber contained 30 microliters of a 5% (w/w) suspension of high density hCG-sensitized latex particles and 40 microliters of the suspending medium. The cuvette rotor was placed in the Multistat III and the absorbance versus time mode was recalled. The reaction was initiated by the mixing of the contents of the two chambers which contained the sample and latex reagents as described above after they had been warmed to a temperature of 37 degrees C. The absorbance at a wavelength of 690 nm was first recorded 3 seconds after initiation of the reaction and recorded at various time intervals thereafter for up to 10 minutes during the continuous rotation of the rotor at 1000 RPM.

As seen in table I, the absorbance decreased rapidly during the first three minutes of centrifugation due to the rapid removal of the dense latex particles from the lightpath. The absorbance readings stabilized after 5 minutes of centrifugation to an absorbance due only to the low density latex particles remaining in suspension.

Absorbance measurements after 5 minutes of centrifugation were greater in samples which contained hCG as compared to samples which did not. A direct relation between the amount of hCG present and the absorbance after 5 minutes was found. Table II represents a standard curve which could be generated from this data in which the absorbance at 690 nm after 5 minutes was linear with respect to the log of the hCG concentration in the serum. The range of this assay is greatly extended as compared to conventional latex agglutination immunoassays for hCG and encompases from 7 to 250 mI.U. per ml hCG in human serum.

TABLE 1

Centrifugation Inhibition Immunoassay
Using Latex Particles of Different Specific Gravities.

| Time of Centrifugation (seconds) | Absorbance at 690 nm | |
| --- | --- | --- |
| hCG/ml | 0 mI.U. hCG/ml | 15 mI.U. |
| 3 | 2.375 | 2.395 |
| 63 | 2.416 | 2.429 |
| 123 | 2.161 | 2.067 |
| 183 | 1.089 | 1.138 |
| 243 | 0.695 | 0.856 |
| 303 | 0.630 | 0.779 |

TABLE II

Standard Curve for hCG in Human Serum

| hCG Concentration in Serum (mI.U./ml) | Absorbance at 690 nm After 5 Minutes |
| --- | --- |
| 0 | 0.630 |
| 8 | 0.754 |
| 15 | 0.779 |
| 31 | 0.795 |
| 63 | 0.808 |
| 125 | 0.841 |
| 250 | 0.868 |

EXAMPLE 2

Digoxigenin tridigitoxoside (digoxin) was covalently coupled to BSA by periodate oxidation followed by stabilization of the Schiff base linkage by reduction with sodium borohydride. The synthesized hapten-protein conjugate was then covalently coupled to high specific gravity latex spheres (sp gr.=1.45, avg. dia.=1.02 μm) by using a carbodiimide coupling reagent. All latex reagents used in this example were suspended in 1% BSA in PBS containing 0.1% sodum azide. Rabbit anti-digoxin polyclonal antibody was adsorbed onto 0.42 μm diameter latex spheres of low specific gravity (1.05) to be used as the complementary reagent in the assay.

In the sample chamber of a cuvette rotor from a Multistat III microscentrifugal analyzer manufactured by Instrumentation Laboratories was placed 65 μl of normal human serum in the presence or absence of various amounts of digoxin. Then, 15 μl of a 0.25% (w/w) suspension of antibody-coated low density latex particles was added to the serum samples. The reagent chamber of the cuvette contained 70 microliters of a 2.8% (w/w) suspension of high density hapten-latex reagent. The reaction was initiated by the mixing of the contents of the cuvette chambers after the rotor had attained 37° C. The optical density was measured at 690 nm every 60 seconds during continuous centrifugation. After 5 minutes, the absorbance in each cuvette was plotted against the concentration of digoxin in the serum.

A direct relationship was found between the concentration of digoxin in the serum and the optical density of the reaction mixture after 5 minutes of centrifugation, as illustrated in Table III. This particular experiment was designed to encompass the therapeutic range for this drug in serum, however the sensitivity of the assay could be adjusted by variation of the amount of antibody-latex reagent used.

TABLE III

Centrifugal Inhibition Immunoassay
Using Particles of Different Specific Gravities
Standard Curve for Digoxin in Human Serum

| Digoxin Concentration in Serum (ng/ml) | Absorbance at 690 nm After 5 Minutes |
| --- | --- |
| 0 | 0.554 |
| 1 | 0.608 |
| 2 | 0.655 |
| 3 | 0.692 |
| 4 | 0.702 |
| 5 | 0.750 |
| 8 | 0.773 |
| 10 | 0.860 |

EXAMPLE 3

Purified C-reactive protein obtained from a commercial supplier was covalently bound to carboxylate-modified high density latex particles (sp gr=1.45) by means of a water soluble carbodiimide coupling reagent. Low density latex was adsorbed with partially purified polyclonal antibody to CRP. All of the latex reagents used in this example were washed and resuspended in 50 mM phosphate pH 7.8, 5 mM EDTA, 0.1% sodium azide and 10 mg/ml BSA.

In the sample chamber of a cuvette rotor designed for use in a Multistat III Plus microcentrifugal analyzer manufactured by Instrumentation Laboratories was placed 40 μl of a 0.25% suspension of low density latex CRP reagent along with 10 μl of CRP containing serum and 30 μl of buffer. The reagent chamber contained 40 μl of a 10% suspension of the high density latex CRP reagent and 30 μl of buffer. The final concentrations after initiation of the reaction by mixing the contents of each chamber were: 0.067% (w/w) low density latex, 2.7% (w/w) high density latex and 0.067% (v/v) human serum in a total volume of 150 μl.

The reaction was begun automatically by the mixing of the contents of the cuvette chambers after the rotor had attained 37° C. The optical density was measured at 690 nm every 60 seconds during continuous centrifugation. After 5 minutes, the absorbance in each cuvette was plotted against the concentration of CRP in the serum.

As illustrated in table IV, a standard curve for CRP in serum could be generated by the high density latex centrifugation assay in a practical range. Basal levels of CRP in normal human serum ranges between 0.1 and 5 μg/ml while CRP-positive sera contain at least 10 μg/ml. The standard curve generated by the present method covers a range of 4 to 23 μg CRP per ml of serum.

TABLE IV

Standard Curve for C-Reactive Protein in Serum

| CRP concentration in serum (ug/ml) | Absorbance at 690 nm After 5 Minutes |
|---|---|
| 0 | 0.911 |
| 4 | 0.991 |
| 9 | 1.106 |
| 13 | 1.118 |
| 18 | 1.196 |
| 24 | 1.214 |

EXAMPLE 4

Latex-based reagents for detecting digoxin were prepared as described in example 2. In each of several glass 10×75 mm test tubes was placed 60 μl of human serum in the presence or absence of various concentrations of digoxin and 20 μl of a 0.15% (w/w) suspension of 0.81 μm diameter, low specific gravity latex particles adsorbed with the corresponding antibody. After adding 70 μl of a 0.71% (w/w) suspension of the appropriate high specific gravity latex, the solution was mixed and allowed to stand at room temperature for five minutes. Then, 1.5 ml of a 10 mg/ml solution of BSA in PBS was added to each tube and the solution inverted several times before centrifuging at approximately 500×g for three minutes using an I.E.C. Clinical desk-top centrifuge with a fixed angle rotor. The resulting supernatant solution was then aspirated into a Stasar III single-beam spectrophotometer manufactured by Gilford Instruments at 360 nm using the suspending buffer alone as the reference.

As indicated in Table V, proportionally greater optical desities (OD) were recorded in tubes which contained greater concentrations of digoxin. From these data a standard curve for digoxin could be generated ranging from 0 to 8 ng/ml by subtracting the OD obtained from samples not containing digoxin from those with digoxin.

TABLE V

Immunoassay with Complementary Particles of Differing Specific Gravities: Measuring Optical Density Outside of the Reaction Vessel

| Digoxin Concentration in Serum (ng/ml) | Absorbance at 360 nm |
|---|---|
| 0 | 0.316 |
| 1 | 0.384 |
| 2 | 0.390 |
| 3 | 0.423 |
| 5 | 0.440 |
| 8 | 0.492 |

What is claimed is:

1. A method for the detection of a target binding pair member in a biological sample which comprises:
   (a) reacting in a liquid phase in a chamber in a centrifugal field:
   (i) the sample to be analyzed,
   (ii) a plurality of first particles bearing on their surface a binding pair member complementary to target binding pair member, and
   (iii) a plurality of second particles bearing on their surface a binding pair member competitive with the target binding pair member for binding sites on the complementary binding pair member;
   the specific gravity of the first and second particles being sufficiently different with respect to the centrifugal field and the specific gravity and viscosity of the liquid phase to cause detectively different rates of migration in the centrifugal field for first particles, for second particles and for first particles bound to second particles;
   (b) detecting the concentration of particles at a locus in the chamber after a specified time of reaction and centrifugation; and
   (c) correlating the concentration of particles over time with the concentration measured after samples of known target binding member amount are reacted in the centrifugal field with the plurality of first particles and plurality of second particles.

2. The method of claim 1 wherein the second particles are of greater specific gravity than the first particles.

3. The method of claim 2 wherein the second particles are provided in a limiting amount relative to the first particles.

4. The method of claim 3 wherein the second particles bear antigen or hapten on their surface and the first particles bear antibody to the antigen or hapten on their surface.

5. The method of claim 4 wherein the target binding member is a hapten.

6. The method of claim 4 wherein the target binding member is an antigen.

7. The method of claim 2 wherein the concentration of particles is measured at a first time before any particles have migrated substantially in the centrifugal field and is measured at a second time after the second particles and the second particles bound to first particles have substantially migrated in the centrifugal field and before substantial migration of unbound first particles has occured.

8. The method of claim 1 wherein the chamber is subjected to the centrifugal field during the reacting step (a) and detecting step (b).

9. The method of claim 1 wherein the chamber is subjected to the centrifugal field during the reacting step (a), but not during the detecting step (b).

10. The method of claim 9 wherein a portion of the reaction mixture is removed from the chamber after the reacting step (a) and at least a specified time period of centrifugation, and the detecting step (b) comprises detecting the concentration of particles in the removed portion.

11. The method of claim 1 wherein the first particles are of greater specific gravity than the second particles or the liquid phase and the first particles bear antigen or hapten on their surface and the second particles bear antibody to the antigen or hapten on their surface.

12. The method of claim 1 wherein the first particles are of greater specific gravity than the second particles and are of greater specific gravity than the liquid phase.

13. The method of claim 12 wherein the target binding member is an antigen or hapten, the first particles bear antibody on their surface and the second particles bear antigen or hapten on their surface.

14. The method of claim 1 wherein the sample is reacted first with the first particles and then with the second particles, whereby the method is an inhibition assay.

15. The method of claim 1 wherein the sample is mixed with the second particles no later than mixing with the first particles, whereby the method is a competition assay.

16. The method of claim 1 wherein a reagent containing first particles, a reagent containing second particles and a sample solution are introduced into at least two chambers of a radially extending cuvette of a rotor, the rotor is spun to mix sample, reagent containing first particles and reagent containing second particles; and the rotor is continually spun to create the centrifugal field.

17. The method of claim 16 wherein the sample and the reagent containing first particles are introduced into one chamber of the radially extending cuvette and the reagent containing second particles is introduced into a second chamber of the radially extending cuvette.

18. The method of claim 1 wherein the liquid phase has substantially the same specific gravity as one of the first and second particles and has substantially greater specific gravity than the other of the first and second particles, whereby the other of the first and second particles floats away from the locus inwardly in the centrifugal field.

* * * * *